United States Patent [19]

Oishi et al.

[11] 4,324,855
[45] Apr. 13, 1982

[54] PROCESS FOR DEVELOPING A SILVER HALIDE EMULSION

[75] Inventors: Yasushi Oishi; Shigeo Hirano, both of Minami-ashigara, Japan

[73] Assignee: Fuji Photo Film Co., Ltd., Kanagawa, Japan

[21] Appl. No.: 140,923

[22] Filed: Apr. 16, 1980

[30] Foreign Application Priority Data

Apr. 17, 1979 [JP] Japan ............... 54-46949

[51] Int. Cl.³ ............... G03C 1/36; G03C 5/24
[52] U.S. Cl. ............... 430/378; 430/375; 430/543; 430/547; 430/410; 430/598; 430/559; 430/390
[58] Field of Search ........... 430/410, 411, 547, 598, 430/596, 541, 543, 374, 378, 559, 390, 375

[56] References Cited

U.S. PATENT DOCUMENTS 3,330,655  7/1967  Salminen ............... 430/598
3,759,901  9/1973  Lincoln et al. ........ 430/598
4,115,122  9/1978  Adachi et al. ......... 430/596

FOREIGN PATENT DOCUMENTS

2628257  1/1977  Fed. Rep. of Germany ...... 430/598

702162  1/1954  United Kingdom ........ 430/598

Primary Examiner—Won H. Louie, Jr.
Attorney, Agent, or Firm—Sughrue, Mion, Zinn, Macpeak and Seas

[57] ABSTRACT

A process for developing a light-sensitive material comprising a support having thereon at least one internal latent image-forming silver halide photographic emulsion layer which comprises, after imagewise exposure, developing the light-sensitive material with an alkaline solution of a developing agent in the presence of a compound represented by the formula I which is capable of selectively forming latent images in the inner portions of said silver halide upon development:

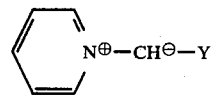

I wherein Y represents an acyl group or a cyano group and said acyl group and the 3-, 4- or 5-position of the pyridinium ring may be optionally substituted.

25 Claims, 2 Drawing Figures

PROCESS FOR DEVELOPING A SILVER HALIDE EMULSION

BACKGROUND OF THE INVENTION

1. Field of the Invention

This invention relates to a process for developing a silver halide photographic emulsion and, more particularly, to a process for developing a silver halide emulsion capable of forming a latent image in the inner portions of silver halide grains, to thereby directly form positive images.

2. Description of the Prior Art

Several photographic processes for directly obtaining positive (reversal) images through one development after imagewise exposure have been known. One of them is a process using a silver halide emulsion capable of forming latent images in the inner portions of the silver halide grains. According to this process, such a silver halide photographic emulsion (herein referred to as an internal latent image-forming silver halide emulsion) is imagewise exposed and subjected to uniform exposure or to the action of a nucleating agent such as hydrazine to form development nuclei on the grain surface, and then processed with a surface developer to obtain positive (reversal) images. This process is called an internal image-reversal process, the principles of which are described in, for example, *The Theory of Photographic Process*, 4th Ed., compiled by T. H. James (1977), p. 187.

The nucleating agent (or fogging agent) used for the internal image-reversal process is incorporated in a developer or a light-sensitive material, in particular, in a silver halide emulsion layer. As the nucleating agent, there are hydrazines such as described in East German Pat. No. 5,024, U.S. Pat. Nos. 2,563,785, 2,588,982, 2,604,440, 3,227,552, 4,030,925, 4,080,207, and *Research Disclosure*, 15164, pp. 76–77 (structural formulae I and II), hetero ring quaternary ammonium compounds such as described in U.S. Pat. Nos. 3,615,615, 3,718,470, 3,719,494, 3,734,738, 3,330,655, and 4,094,683. However, conventional nucleating agents have one or more defects especially when they are incorporated in a silver halide emulsion layer. They may not provide good photographic properties (in particular, a high Dmax/Dmin ratio), they may reduce the storage stability of the silver halide emulsion, negative images are liable to form particularly in high exposure portions, gases are generated upon photograhic processing which results in deterioration of image uniformity, the compounds lose their activity under some conditions due to their instability, they are liable to react with other emulsion additives and lose their activity, stain is formed in highlight exposure portions, a long induction period is required upon development or a sufficient developing rate is not attained, and synthesis of the compounds in the pure form is difficult.

SUMMARY OF THE INVENTION

One object of the present invention is to provide a reversal development process to form images with good photographic properties, in particular, high Dmax and low Dmin using imagewise exposed, internal latent image-forming silver halide emulsions.

Another object of the present invention is to provide a process for forming reversal images, which comprises incorporating a nucleating agent in a light-sensitive material in a stable form and processing the light-sensitive material with an alkaline aqueous solution of a developing agent to obtain constant results.

A further object of the present invention is to provide a process for forming reversal images by processing a light-sensitive material with an alkaline aqueous solution of a developing agent containing a nucleating agent.

Still a further object of the present invention is to provide a process for forming color reversal images by processing a light-sensitive material having a coupler-containing silver halide emulsion layer with an alkaline aqueous solution of a developing agent in the presence of a nucleating agent.

Another object of the present invention is to provide transferred color reversal images by processing a light-sensitive material having an internal latent image-forming silver halide emulsion layer associated with a dye image-forming material capable of forming transferred images of a diffusible dye with an alkaline aqueous solution of a developing agent in the presence of a nucleating agent.

Other objects of the present invention will be apparent from the following detailed description of the invention.

DETAILED DESCRIPTION OF THE INVENTION

It has now been discovered that the above-described objects of the present invention are attained by conducting development of an imagewise exposed light-sensitive material comprising a support having provided thereon at least one internal latent image-forming silver halide photographic emulsion layer with an alkaline solution of a developing agent in the presence of a pyridinium ylide, in particular, a compound of the formula I:

wherein Y represents an aromatic (preferably) or aliphatic acyl group containing from 2 to 30 carbon atoms or a cyano group, said acyl group and the 3-, 4- or 5-position of the pyridinium ring being optionally substituted.

The compounds of the formula I are formed during development from pyridinium salts. Accordingly, as a preferred embodiment the present invention is a process for obtaining reversal images by processing a light-sensitive material comprising a support having provided thereon at least one internal latent image-forming silver halide photographic emulsion layer associated with a compound of the formula II:

wherein Y is defined as in the formula I, and $X^{\ominus}$ represents an anion.

Preferred salts capable of providing the above-described zwitter-ion (formula I) known as an N-ylide under alkaline conditions are represented by the formulae III and IV:

In the above formulae, n represents an integer of 0, 1, 2 or 3, $R^1$ represents a substituent at the 3-, 4- or 5-position selected from a trihalomethyl group, a cyano group, a carbamoyl group, a carboxylic acid ester group, a carbonamido group, a sulfonamido group, an acyl group, a sulfonyl group, a sulfamoyl group, an acylamino group, an aryl group, a non-α-hydrogen-containing alkyl group, an alkenyl group, and a heterocyclic ring, or a substituent at 3- or 5-position selected from an α-hydrogen-containing alkyl group and a halogen atom (e.g., F, Cl, Br) and, where two or more $R^1$ are present they may be the same or different. Suitable $R^1$ substituents are described in more detail below with respect to the compounds of the formula III and IV.

$R^2$ represents a mono-, di- or tricyclic aryl group containing 6 to 29 carbon atoms, a 5- or 6-membered heterocyclic group containing an oxygen atom, a sulfur atom or a nitrogen atom as the hetero atom (for example, a thienyl group or a straight chain, branched chain or cyclic alkyl group containing 1 to 29 carbon atoms.

Furthermore, $R^1$ and $R^2$ can represent a polyvalent residue or a polymer residue in which two or more of the above-described substituents are bound together through one or more linking groups resulting in compounds such as Also, $R^1$ and $R^2$ may represent a residue bearing a hydrophobic ballast group containing 8 or more carbon atoms. Two adjacent $R^1$'s may combine a 5- or 6-membered aromatic ring. A ballast group is a hydrophobic group having an alkyl or an alkylaryl group containing 8 to about 30 carbon atoms, such as an octyl group and a dodecyl group.

As described in W. G. Phillips, J. Org. Chem., 35, p. 3144, the hydrogen atom on the methylene group sandwiched between the pyridinium nitrogen and the cyano or acyl group in the compound represented by the general formula III or IV can be ionized to a proton to provide a reactive N-ylide represented by the formula I. The mechanism whereby the compounds of the formula III or IV cause or accelerate reversal development of internal latent image-forming emulsions is not clear but, because the pKa value of the compounds is near or below the pH of the developer used, it is believed that the compound functions in a dissociated form or an active form derived therefrom. In its dissociated form, it is understood the compound of the formula I exists in tautomers as represented by the following formulae:

As the compounds used in the present invention, those which are mainly in an undissociated form with an extremely low activity when incorporated in a lightsensitive material which is in a weakly acidic or neutral condition and which under the alkaline conditions of development processing are converted to a highly active dissociated form are advantageously used. In general, those compounds which have an active methylene group having an acidity corresponding to a pKa value of not less than about 6.0, preferably not less than about 7.0, and more preferably not more than about 11 are suitable depending upon such factors as the type of light-sensitive material, developing conditions, etc. The acidity (pKa) can be adjusted by properly selecting the sibstituents $R^1$ and $R^2$ in the formulae III and IV.

The compounds used in the present invention are distinguished from the aforesaid known heterocyclic quaternary ammonium salts described in U.S. Pat. Nos. 3,615,615, 3,718,470, 3,719,494, 3,734,738, 3,330,655 and 4,094,683, in several respects. First, there is the structural difference, while an alkylene group containing two or more carbon atoms such as —CH$_2$CH$_2$—intervenes between the heterocyclic quaternary ammonium nitrogen atom and the activating group in known compounds with the existence of such alkylene group being necessary for functioning as a nucleating agent, the compounds of the present invention contain a methylene group between the activating acyl group and the heterocyclic quaternary ammonium nitrogen atom. Second, while the structural moiety of known quaternary ammonium salts being necessary for functioning as a nucleating agent does not substantially undergo change between neutrality and alkalinity, whereas the compounds of the present invention are dissociated in a manner closely related to their function as nucleating agents which clearly distinguishes the compounds of the present invention from known compounds.

West German Patent Application (OLS) No. 2,448,432 describes compounds having structure analogous to the compounds in the present invention. However, the compounds described in West German Patent Application (OLS) No. 2,448,432, particularly 2-bromo-1-phenacyl pyridinium bromide, have a halogen atom at 2-position of the pyridinium ring which reacts with gelatin. The compounds fail to exhibit any nucleating action on internal latent imageforming silver halide emulsions upon development.

The process of this invention produces reversal images with high maximum density (Dmax) and low minimum density (Dmin). This means that a high proportion of the silver halide contained in the light-sensitive material is converted to silver image and, as a result, economical and resource-saving advantages are realized in a reduction in the amount of silver halide contained in the light-sensitive material and an improvement in photographic properties, i.e., an improvement in image sharpness and in shortening the photographic processing time due to a reduction in the thickness of the emulsion layer.

The process of the present invention enables one to obtain the reversal image providing effect described above using a nucleating agent in only a small amount and hence secondary effects accompanying the use of the nucleating agent, such as the formation of stain, can be limited to a low level.

The process of the invention enables reversal development in a short time. The compounds of the present invention can be incorporated in a photographic emulsion layer without adversely affecting the stability of the layer.

The process of the present invention completely eliminates the formation of development mottles due to generation of gas upon formation of the reversal image such as generation of nitrogen gas as is experienced with hydrazine compounds.

Further, the compounds of the present invention can be easily prepared and handled in stable form, as described herein.

Other characteristic aspects of the present invention will become apparent from the following detailed descriptions and Examples.

The internal latent image-forming silver halide emulsion used in the present invention has a light-sensitive center mainly within the silver halide grains and, upon imagewise exposure, a latent image is selectively formed therein but, a latent image is only scarcely formed on the surface of the grains. Such an internal latent image-forming silver halide emulsion is characterized by a silver image density obtained upon developing, with a surface developer according to James, supra, pp. 171–176 (corresponding to surface latent image) which is distinctly lower than the silver image density obtained using an internal developer (corresponding to total latent image).

An internal latent image type of silver halide emulsion can be defined as one which, when a test portion is exposed to a light intensity scale for a fixed time up to about 1 second and developed for 4 minutes at 20° C. in an ordinary surface developer, one which develops an image only on the surface of the grains of an internal latent image emulsion, which developer type is exemplified by one having the formula:

| | |
|---|---|
| p-Hydroxyphenylglycine | 10 g |
| Sodium carbonate (crystals) | 100 g |
| Water to 1 liter | | exhibits a maximum density not greater than 1/5 the maximum density obtained when the same emulsion is equally exposed and developed for 3 minutes at 20° C. in an internal type developer, one which develops an image inside the grains of an internal latent image emulsion, which developer type is exemplified by one having the formula:

| | |
|---|---|
| Hydroquinone | 15 g |
| Monomethyl-p-aminophenol sulfate | 15 g |
| Sodium sulfite (anhyd) | 50 g |
| Potassium bromide | 10 g |
| Sodium hydroxide | 25 g |
| Sodium thiosulfate (crystals) | 20 g |
| Water to 1 liter | |

Preferably the maximum density obtained with the surface developer is not greater than 1/10 the maximum density obtained when the same emulsion is developed in the internal type developer. Stated conversely, an internal latent image emulsion, when developed in an internal type developer exhibits a maximum density at least 5 and preferably at least 10 times the maximum density obtained when the emulsion is exposed in the same way and developed in a surface developer.

Internal latent image-forming silver halide emulsions can be prepared by various processes. For example, Burton's emulsions containing a high iodide content are prepared by an ammoniacal process according to E. J. Wall, *Photographic Emulsions*, pp. 35–36 and 52–53 (American Photographic Publishing Co. (1929)) and U.S. Pat. Nos. 2,497,875 and 2,563,785; large grained primitive emulsions containing iodide in a low content can be prepared by an ammoniacal process according to West German Patent Application (OLS) No. 2,728,108; other emulsions can be prepared by rapidly reducing the concentration of ammonia in a silver halide-ammonia complex salt solution to thereby precipitate silver halide grains according to U.S. Pat. No. 3,511,662; conversion emulsions can be obtained by catastrophe precipitation by first forming silver salt grains with high solubility such as silver chloride grains and then converting to a silver salt with low solubility such as silver bromoiodide according to U.S. Pat. No. 2,592,250; core-shell type emulsions can be prepared by mixing a fine grained emulsion with a chemically sensitized large grained core emulsion and ripening it to form a silver halide shell on the core grains according to U.S. Pat. No. 3,206,313 and British Pat. No. 1,011,062; core-shell type emulsions can also be prepared by adding a soluble salt solution and a soluble halide solution to a chemically sensitized monodisperse core emulsion while maintaining the silver ion concentration at a definite level thus forming a silver halide shell on core grains according to British Pat. No. 1,027,146 and U.S. Pat. No. 3,761,276; halide-localized emulsions containing grains having a two or mono layer structure wherein the first layer and the second layer have different halide compositions are prepared according to U.S. Pat. No. 3,935,014; emulsions can be prepared by forming silver halide grains in an acidic medium containing a trivalent metal ion to thereby incorporate a different metal therein according to U.S. Pat. No. 3,447,927, and the like. These internal latent image-forming emulsions can be used in practicing the present invention.

The developing agent used in the present invention can be selected from a wide variety of developing agents heretofore used for silver halide emulsions. 1,2- or 1,4-dihydroxybenzene, ascorbic acid, reductic acid and the derivatives thereof, 2- or 4-sulfonamidophenol and the derivatives thereof, 2- or 4-aminophenol and the derivatives thereof, 1,4-phenylenediamines (particularly the derivatives described in U.S. Pat. No. 2,507,154), 1-phenyl-3-pyrazolidone and the derivatives thereof, and hydroxylamine and derivatives thereof are advantageously used. Specific examples are described in James, supra, Chapter 11. These developing agents may be used alone or in combinations of two or more, especially in a super-additive combination. Where an immobilized reducing agent such as a ballast group-containing diffusion-resistant hydroquinone derivative or dye-releasing redox (DRR) compound is incorporated in a light-sensitive material and the developing agent behaves as an agent of transferring electrons between the silver halide and the immobilized reducing agent, the developing agent is advantageously selected from aminophenols such as p-methylaminophenol; pyrazolidones such as 1-phenyl-4-methyl-4-hydroxymethyl-3-pyrazolidone, 1-phenyl-4,4-bis(hydroxymethyl)-3-pyrazolidone, 1-phenyl-4,4-dimethyl-3-pyrazolidone, etc.; and p-phenylenediamines such as N,N,N',N'-tetramethyl-p-phenylenediamine, etc. The developing agent can be incorporated in any of a developer, a light-sensitive material, and a third member contacted with the light-sensitive material upon development (e.g., a rupturable container). The developing agent may be incorporated in the form of a precursor.

The developer also contains a base such as sodium hydroxide, potassium hydroxide, sodium carbonate or sodium phosphate and has an alkalinity of not less than about 9, preferably not less than about 10, in pH. The developer further contains an antioxidant such as sodium sulfite, ascorbic acid or piperidinohexose reductone, and may contain a silver ion concentration-controlling agent such as potassium bromide.

Of the compounds represented by the formulae III and IV, those which are advantageously used in the practice of the present invention are compounds having an electron attracting group at the meta position (the 3- or 5-position) of the pyridinium ring. For example, the presence of substituents such as a halogen atom (e.g., a fluorine atom, a chlorine atom, a bromine atom or an iodine atom); a trihalomethyl group; a cyano group; a carbamoyl group of the formula —CONR$^3$R$^4$ (wherein R$^3$ and R$^4$ each represents a hydrogen atom, an alkyl (e.g., methyl, ethyl, (n)octyl) group, an aryl (including mono- and bicyclic aryl groups, such as phenyl, (i.e., 3-(n-tetradecyloxy)phenyl), and (i.e., 3-(n-tetradecyloxycarbonyl)phenyl)) group or a heterocyclic ring (e.g., thienyl), the alkyl group, aryl group and heterocyclic ring containing 1 to about 20 carbon atoms and being optionally substituted (for example, substituents for the alkyl group include a hydroxy group, a cyano group and an alkoxy group containing 1 to 4 carbon atoms and substituents for the aryl group include a hydroxy group, a cyano group, an alkyl group containing 1 to 4 carbon atoms, an alkoxy group containing 1 to 4 carbon atoms and a halogen atom (e.g., F, Cl, Br)), or R$^3$ and R$^4$ may combine to form a 5- or 6-membered alicyclic ring (such as piperidino, morpholino, etc.) together with the nitrogen atom); a carboxylic acid ester group of the formula —COOR$^5$ (wherein R$^5$ represents an alkyl group, an aryl group or a saturated or unsaturated 5- or 6-membered heterocyclic ring group, which may contain 2 or more hetero atoms of O, S, or N, with the alkyl group, aryl group, and heterocyclic ring containing up to about 20 carbon atoms and being optionally substituted with substituents such as a halogen atom, an alkyl group, an alkoxy group, an aryloxy group, an acylamino group, etc.); a carbonamido group of the formula —NHCOR$^{13}$ (wherein R$^{13}$ represents an alkyl group containing 1 to 21 carbon atoms or an aryl group containing 6 to 20 carbon atoms); a sulfonamido group of the formula —NHSO$_2$R$^{14}$ (wherein R$^{14}$ represents an aryl group containing 6 to 20 carbon atoms); an aryl group containing 6 to 20 carbon atoms; an alkyl group containing 1 to 22 carbon atoms; an alkenyl group containing 2 to 10 carbon atoms; a 5- or 6-membered nitrogen-containing heterocyclic ring, which can also contain a second hetero atom (such as an oxygen atom, a nitrogen atom, a sulfur atom or a selenium atom); an acyl group of the formula —COR$^6$ (wherein R$^6$ represents a hydrogen atom, a hydroxy group, an alkyl group, an aryl group, a heterocyclic ring as in R$^3$ and R$^4$, an amino group, an alkoxy group, an aryloxy group or a heterocyclic oxy group, with the alkyl group, the alkoxy group, the aryl group, the aryloxy group and the heterocyclic ring containing up to about 20 carbon atoms and being optionally substituted by a halogen atom, an alkyl group, an alkoxy group, an aryloxy group, an acylamino group, etc.); a sulfamoyl group of the formula —SO$_2$NR$^3$R$^4$ (wherein R$^3$ and R$^4$ are defined as above); a sulfonyl group of the formula —SO$_2$R$^6$ (wherein R$^6$ is defined as above); or an acylamino group of the formula —NHCOR$^7$ (wherein R$^7$ represents an alkyl group, an aryl group, a heterocyclic ring as in R$^3$ and R$^4$ or an amino group, with the alkyl group, aryl group, heterocyclic ring group, and amino group containing up to about 20 carbon atoms and optionally substituted with an alkyl group (e.g., a methyl group, an ethyl group, a butyl group, an octyl group, a dodecyl group, etc.) and/or an aryl group (e.g., a phenyl group, a tolyl group, a naphthyl group, etc.)) is advantageous.

Pyridinium rings having a carbonyl-containing substituent group or a cyano group at the 3-position are particularly useful in the present invention and can be selected from the pyridinium rings derived from 3-substituted pyridines described in Pyridine and its Derivatives, Part III, Chapter 10, compiled by E. Klingsberg, Interscience Publishers (1962), pp. 252–263 and 272–282.

Of the compounds represented by the general formula III, those which are particularly advantageous in the practice of the present invention are compounds wherein R$^2$ represents an aryl group or an aromatic heterocyclic ring such as a phenyl group, a naphthyl group, a thienyl group, or a furyl group. Of these substituents, a phenyl group or a substituted phenyl group is excellent from the point of view of its synthesis. As substituents for the phenyl group, a halogen atom such as a fluorine atom, a chlorine atom or a bromine atom;

an alkyl group containing 1 to about 20 carbon atoms such as a methyl group, an ethyl group, a propyl group, a t-butyl group, a t-amyl group or an octyl group; an alkoxy group containing 1 to about 20 carbon atoms such as a methoxy group, an ethoxy group, an isopropyloxy group, a benzyloxy group, an octyloxy group, a dodecyloxy group or a hexadecyloxy group; an aryloxy group containing 6 to about 25 carbon atoms such as a phenyloxy group or a 3-pentadecylphenyloxy group; or an acylamino group represented by —NHCOR$^8$ or —NHSO$_2$R$^8$ (wherein R$^8$ represents an alkyl group, an aryl group, a heterocyclic ring or an amino group, with the alkyl group, aryl group, heterocyclic ring(as in the case of R$^3$ or R$^4$), and amino group containing up to about 20 carbon atoms and being optionally substituted with an alkyl group containing 1 to 10 carbon atoms) are advantageous.

The alkyl group represented by R$^8$ may contain 1 to about 20 carbon atoms and includes, for example, a methyl group, an ethyl group, a butyl group, an octyl group, a dodecyl group, etc. The aryl group represented by R$^8$ may contain 6 to about 20 carbon atoms and includes, for example, a phenyl group, a tolyl group, a naphthyl group, etc. The amino group represented by R$^8$ may be substituted by an alkyl group (e.g., a methyl group, an ethyl group, a butyl group, an octyl group, a dodecyl group, etc.) or an aryl group (e.g., a phenyl group, a tolyl group, a naphthyl group, etc.).

The anion represented by X$^\oplus$ in the general formulae III and IV can be selected from a wide range of anions. It may be easily understood that the anion, as a counter ion, is not limited as long as it does not adversely influence photographic properties, because it is to be easily exchanged with other anions contained in the photographic layer or a processing composition upon practicing the present invention and because, under developing conditions, it is eliminated from the functioning ylide. While chloride, bromide, and iodide ions are illustrated in the description of the present invention for convenience, inorganic anions such as a nitrate ion, a sulfate ion, a perchlorate ion, etc., and organic anions such as a fatty acid ion, a toluenesulfonate ion, a methanesulfonate ion, a picrate ion, etc., can similarly be used.

Specific examples of the compounds advantageously used in the present invention are illustrated below.

Compound 1

Compound 2

Compound 3

Compound 4

Compound 5

Compound 6

Compound 7

Compound 8

Compound 9

Compound 10

Compound 11

Compound 12

Compound 13

Compound 14

Compound 15

Compound 16

Compound 17

Compound 18

Compound 19

Compound 20

Compound 21

Compound 22

-continued

Compound 23: pyridinium-CH₂CO-C₆H₃(C₂H₅)(C₅H₁₁(t))-NHCOCH-O-C₆H₃(C₅H₁₁(t))(C₅H₁₁(t)) · Br⁻

Compound 24: pyridinium-CH₂CO-C₆H₄-F · Br⁻

Compound 25: pyridinium-CH₂CO-C₆H₄-Cl · Br⁻

Compound 26: pyridinium-CH₂CO-C₆H₄-Cl · Br⁻

Compound 27: pyridinium-CH₂CO-C₆H₄-Br · Br⁻

Compound 28: pyridinium-CH₂CO-C₆H₂(CH₃)₃ · I⁻

Compound 29: pyridinium-CH₂CO-naphthyl · I⁻

Compound 30: pyridinium-CH₂CO-phenanthryl · I⁻

Compound 31: pyridinium-CH₂CO-thienyl · Br⁻

Compound 32: (CH₃-thiazolyl)-pyridinium-CH₂CO-C₆H₅ · Br⁻

Compound 33: (C₁₂H₂₅-thiazolyl)-pyridinium-CH₂CO-C₆H₅ · Br⁻

Compound 34: (phenyl-thiazolyl)-pyridinium-CH₂CO-C₆H₅ · Br⁻

Compound 35: (Cl)-pyridinium-CH₂CO-C₆H₅ · Br⁻

Compound 36: (Cl,Cl)-pyridinium-CH₂CO-C₆H₅ · Br⁻

Compound 37: (Br)-pyridinium-CH₂CO-C₆H₅ · Br⁻

Compound 38: (NC)-pyridinium-CH₂CO-C₆H₅ · Br⁻

Compound 39: (NC)-pyridinium-CH₂CO-C₆H₄-NHCOC₁₅H₃₁(n) · Br⁻

Compound 40: (NC)-pyridinium-CH₂CO-C₆H₃(C₂H₅)(C₅H₁₁(t))-NHCOCH-O-C₆H₃(C₅H₁₁(t))(C₅H₁₁(t)) · Br⁻

Compound 41: (NC)-pyridinium-CH₂CO-C₆H₄-CH₃ · Br⁻

Compound 42: (NC)-pyridinium-CH₂CO-C₆H₄-OCH₃ · Br⁻

Compound 43: (NC)-pyridinium-CH₂CO-C₆H₄-OC₁₆H₃₃ · Br⁻

Compound 44: (H₂NCO)-pyridinium-CH₂CO-C₆H₅ · Br⁻

Compound 45: (H₂NCO)-pyridinium-CH₂CO-C₆H₄-CH₃ · Br⁻

Compound 46: (H₂NCO)-pyridinium-CH₂CO-C₆H₄-OCH₃ · Br⁻

Compound 47: (H₂NCO)-pyridinium-CH₂CO-C₆H₄-OC₁₆H₃₃(n) · Br⁻

Compound 48: (CH₃NHCO)-pyridinium-CH₂CO-C₆H₅ · Br⁻

-continued

Compound 49: (C2H5)2N-CO-O-[pyridinium-3-yl]-N⊕-CH2CO-C6H5 · Br⊖

Compound 50: C6H5-NH-CO-O-[pyridinium-3-yl]-N⊕-CH2CO-C6H5 · Br⊖

Compound 51: H2NCO-O-[pyridinium-3-yl]-N⊕-CH2CO-C6H4-C5H11(t) · Br⊖

Compound 52: H2NCO-O-[pyridinium-3-yl]-N⊕-CH2CO-C6H4-NHCOC15H31(n) · Br⊖

Compound 53: H2NCO-O-[pyridinium-3-yl]-N⊕-CH2CO-C6H4-NHCOCH(C2H5)O-C6H4-C5H11(t) · Br⊖

Compound 54: (n)C8H17NHCO-[pyridinium-3-yl]-N⊕-CH2CO-C6H5 · Br⊖

Compound 55: (t)C5H11-C6H3(C5H11(t))-O(CH2)4NHCO-[pyridinium-3-yl]-N⊕-CH2CO-C6H4-OCH3 · Br⊖

Compound 56: (n)C16H33NHCO-[pyridinium-3-yl]-N⊕-CH2CO-C6H5 · Br⊖

Compound 57: C6H5-COCH2-N⊕[pyridinium]-CONHCH2NHCO-[pyridinium]-N⊕-CH2CO-C6H5 · 2Br⊖

Compound 58: C2H5OOC-[pyridinium-3-yl]-N⊕-CH2CO-C6H5 · Br⊖

Compound 59: (n)C4H9OOC-[pyridinium-3-yl]-N⊕-CH2CO-C6H5 · Br⊖

Compound 60: (n)C8H17OOC-[pyridinium-3-yl]-N⊕-CH2CO-C6H5 · Br⊖

Compound 61: C6H5-CH2OOC-[pyridinium-3-yl]-N⊕-CH2CO-C6H5 · Br⊖

Compound 62: (C2H5)2N-CO-[pyridinium-4-yl]-N⊕-CH2CO-C6H5 · Br⊖

Compound 63: CH3CO-O-[pyridinium-3-yl]-N⊕-CH2CO-C6H5 · Br⊖

Compound 64: C6H5-CO-O-[pyridinium-3-yl]-N⊕-CH2CO-C6H5 · Br⊖

Compound 65: CH3CONH-[pyridinium-3-yl]-N⊕-CH2CO-C6H5 · Br⊖

Compound 66: (n)C6H13CONH-[pyridinium-3-yl]-N⊕-CH2CO-C6H5 · Br⊖

Compound 67: H2NCO-[pyridinium-4-yl]-N⊕-CH2CO-C6H5 · Br⊖

Compound 68: NC-[pyridinium-4-yl]-N⊕-CH2CO-C6H5 · Br⊖

Compound 69: C6H5-COCH2SO2-[pyridinium-3-yl]-N⊕-CH2CO-C6H5 · Br⊖

Compound 70: (t)C4H9NHSO2-[pyridinium-3-yl]-N⊕-CH2CO-C6H5 · Br⊖

Compound 71: CH3-[pyridinium-3-yl]-N⊕-CH2CO-C6H5 · Br⊖

Compound 72: C6H5-NHCONH-[pyridinium-3-yl]-N⊕-CH2CO-C6H5 · Br⊖

Compound 73: (t)C4H9-[pyridinium-4-yl]-N⊕-CH2CO-C6H5 · Br⊖

Compound 74: CH2=CH-[pyridinium-4-yl]-N⊕-CH2CO-C6H5 · Br⊖

Compound 75

Compound 77

Compound 79

Compound 81

Compound 83

-continued

Compound 76

Compound 78

Compound 80

Compound 82

Compound 84

The compounds which are particularly preferred for use in the present invention can be represented by the following formulae V and VI:

wherein $R^{10}$ represents a hydrogen atom, an alkyl group containing 1 to 24 carbon atoms (e.g., methyl group, ethyl group), an aryl group containing 6 to 20 carbon atoms (e.g., phenyl group), a heterocyclic group containing 4 to 20 carbon atoms, an amino group of the formula —$NR^3R^4$ (wherein $R^3$ and $R^4$ are defined in the formulae III and IV) (e.g., diethylamino group), an alkoxy group containing 1 to 24 carbon atoms (e.g., ethoxy group), an aryloxy group containing 6 to 20 carbon atoms (e.g., phenoxy group) or a heterocyclic oxy group containing 4 to 20 carbon atoms; $R^{11}$ represents a hydrogen atom, a halogen atom (e.g., F, Cl, Br), an alkyl group containing 1 to 24 carbon atoms (e.g., methyl group), an alkoxy group containing 1 to 24 carbon atoms (e.g., methoxy group, —$OC_{16}H_{33}$ group) or an acylamino group containing 2 to 24 carbon atoms (e.g., —$NHCOCH_3$ group, —$NHCOC_7H_{15}$ group, —$NHCOC_{15}H_{31}$ group); $R^{12}$ represents a cyano group, a halogen atom (e.g., F, Cl, Br) or a trihalomethyl group; X represents an anion; and m is an integer of 1 to 5.

β-Ketopyridinium salts providing the pyridinium ylide compounds used in the present invention are known compounds and can be synthesized according to well known processes. For example, an α-haloketone can be reacted with a pyridine compound as described by F. Kröhke, Chem. Ber., 68, 1177–95 (1935). Another process involves reacting iodine with a ketone compound and a pyridine compound as described by L. C. King, Journal of the American Chemical Society, 66, 894–5 (1944). Alternatively, a diazoketone can be reacted with pyridine as described by L. C. King, Journal of the American Chemical Society, 70, 4154–5 (1948). The anion for the pyridinium can be exchanged by reacting a free acid like perchloric acid in an excess amount of the halide or reacting an equivalent amount of soluble silver salt like silver nitrate using an ion-exchange resin or by precipitating the ylide using sodium carbonate and then neutralizing with an acid. Several processes for synthesizing β-ketopyridinium salts which can be used to advantage in the present invention are also described in W. G. Phillips et al, supra; J. L. Hartwell et al, *Journal of the American Chemical Society*, 68, 868–70 (1946), L. C. King et al, *Journal of the American Chemical Society*, 70, 239–40 (1948), and *N-Ylide Chemistry* by I. Zugravescu et al, MaGraw Hill (1976).

SYNTHESIS EXAMPLE

(1) N-Hexadecylnicotinamide 30.7 g of cetylamine and 33.2 g of pyridine were dispersed in 200 ml of acetonitrile, and 25 g of nicotinic acid chloride hydrochloride was added thereto under cooling with water. After reacting for 3 hours at 55° C., 800 ml of water was added thereto. The thus formed crystals were collected by filtration. Recrystallization from 500 ml of ethanol yielded 36.3 g of the end product. m.p. 85°–87° C.

Elemental Analysis for $C_{22}H_{38}N_2O$: Found (%): C: 76.1; H: 11.1; N: 8.0; Calculated (%): C: 76.3; H: 11.1; N: 8.1.

(2) 3-N-Hexadecylcarbamoyl-1-phenacylpyridinium bromide (Compound 54)

10.4 g of N-hexadecylnicotinamide was reacted with 6.0 g of phenacyl bromide in 100 ml of benzene at 80° C. for 7 hours. Crystals were formed upon cooling the reaction solution. After adding 100 ml of hexane thereto to crystallize, the end product was collected by filtration. Yield: 54.4 g; m.p. 110°–127° C. (flowing point).

Elemental Analysis for $C_{30}H_{45}BrN_2O_2$: Found (%): C: 65.7; H: 8.4; N: 5.3; Calculated (%): C: 66.0; H: 8.3; N: 5.1.

In the present invention, the β-ketopyridinium salt capable of providing the pyridinium ylide may be directly incorporated in an internal latent image-forming emulsion layer or a hydrophilic colloidal layer adjacent to such an emulsion layer. Further, it may be incorporated in an element which is contacted with the emulsion layer upon development such as a spreading sheet in a diffusion transfer film unit. The amount of β-ketopyridinium salt capable of providing the pyridinium ylide varies greatly depending upon the type and properties of the emulsion and upon the compositions of the processing solutions but, in general, the salt can be used in an amount of about $1\times10^{-4}$ mol to $6\times10^{-3}$ mol, preferably about $3\times10^{-4}$ mol to $3\times10^{31\,3}$ mol, per mol of silver halide.

The present invention can be practiced more advantageously using other compounds which enhance direct reversal development of internal latent image-forming type emulsions in combination with the pyridinium salts. For example, triazole compounds such as described in U.S. Pat. No. 2,497,917 or tetrazole compounds such as described in U.S. Pat. No. 3,352,672 facilitate simultaneous achievement of low Dmin and high Dmax. Iodide ion-providing compounds such as described in British Pat. Nos. 1,151,363, 1,187,029, and 1,195,837 serve to provide high Dmax. In addition, active sulfur compounds such as linear or cyclic thiourea derivatives or precursors thereof can accelerate reversal development particularly at low temperatures.

In the present invention, conventionally known nucleating agents such as hydrazide compounds or quaternary ammonium compounds can be used in combination with the β-ketopyridinium compounds capable of providing the pyridinium ylides. In addition, hydroquinones such as tetramethylhydroquinone, tetramethoxyhydroquinone, t-octylhydroquinone, 2-sec-octadecyl-5-sulfohydroquinone, 2-N-morpholil-5-t-octylhydroquinone, etc., and the precursors thereof such as o-acylated products, oxines or bis-oxines accelerate nucleating action upon development.

Images obtained by the present invention are utilized as black-and-white photographic silver images or as color images formed by oxidation with silver halide. Various dye image-providing compounds can be utilized for the formation of color images. Above all, a combination of a primary amine developing agent and a coupler, a dye-releaser (e.g., DRR compounds) capable of releasing a diffusible dye as a result of oxidation upon development, and the like are particularly useful.

As the couplers used in the practice of the present invention, compounds which have a phenolic active hydrogen atom and the compounds having an active methylene group as described in T. H. James, supra, Chapter 12 (particularly pages 353–361), such as phenols, naphthols, pyrazolones, acylacetanilides, benzisoxazolones, pyrazolobenzimidazoles, pyrazolotriazoles, indazolones, etc. These couplers advantageously contain a hydrophobic group such as an alkyl group or an alkylaryl group containing 8 or more carbon atoms as a diffusion-resistant (ballast) group, and one hydrogen atom at the active site thereof is advantageously substituted with a residue capable of being eliminated upon oxidation product of a color developing agent.

In the present invention, various dye-providing materials are associated with direct reversal emulsions to obtain color images through the diffusion transfer process. Those compounds which contain a diffusion-resistant group as described above and which are capable of releasing a diffusible dye by reaction with an oxidized developing agent are particularly advantageous. As such compounds, there are illustrated DDR couplers suited for use with a p-phenylenediamine developing agent (U.S. Pat. No. 3,227,550), amidrazone compounds such as described in Japanese Patent Publication No. 39165/73, compounds capable of releasing a dye by oxidative cyclization such as described in Japanese Patent Publication No. 32129/73, and DRR compounds capable of releasing a dye by crossoxidation and cleavage such as described in U.S. Pat. Nos. 3,928,312, 3,993,638, 4,055,428, and German Patent Application (OLS) No. 2,645,656. The above-described direct reversal emulsions providing dye images can be used in so-called peel-apart and integrated diffusion transfer film units.

The light-sensitive materials used in the present invention can be constructed on various supports such as glass, paper, film base (e.g., polyacrylate film base, polystyrene film base, polycarbonate film base, polyethylene terephthalate film base, and cellulose acetate film base), etc.

The present invention will now be described in more detail by the following non-limiting examples of preferred embodiments of the present invention.

EXAMPLE 1

On a transparent cellulose triacetate film base was coated a first layer containing 0.64 g/m² of a magenta dye-releasing redox compound ($M_1$), 0.2 g/m² of N,N-diethyllaurylamide, and 1.3 g/m² of gelatin. Then, an emulsion completed by adding in order solutions of optical sensitizers $S_1$ and $S_2$, a solution of nucleating agent shown below, and 2-sulfo-5-n-pentadecylhydroquinone potassium salt (0.023 mol/mol Ag) to 100 g of an internal latent image-forming silver halide emulsion containing 60 mmol of regular octahedral silver bromide grains having a particle size of about 1.3μ, and 5.5 g of gelatin, was coated on the first layer in an amount of 1.55 g Ag/m² to form a second layer. Further, a protective layer containing 0.2 g/m² of 2,5-di-t-dodecylhydroquinone and 1.3 g/m² of gelatin was coated thereon to complete a light-sensitive element.

On the other hand, on a transparent polyethylene terephthalate film base was coated a mordant layer containing 3.0 g/m² of poly-(3- or 4-tri-n-hexylammoniummethyl)styrene chloride and 3.0 g/m² of gelatin to prepare an image-receiving element.

The light-sensitive element was subjected to stepwise exposure for sensitometry, and was placed face to face with the image-receiving element, followed by spreading a processing solution between the two elements in a liquid thickness of 80μ. After 3 minutes at 25° C., the image-receiving element was delaminated, neutralized in a 1% acetic acid bath, washed with water for 5 minutes, then dried to obtain a magenta color positive image. On the other hand, the remaining light-sensitive element was fixed with a sodium thiosulfate solution, washed with water, and dried to obtain superposed images wherein a positive silver image and a negative image of remaining color material were superposed one over the other.

In this example, the light-sensitive element and the image-receiving element were hardened with 4,6-dichloro-2-hydroxy-s-triazine sodium salt and formaldehyde, respectively.

The processing solution used had the following composition.

| Carboxymethyl Cellulose Sodium Salt | 60 g |
|---|---|
| Sodium Acid Sulfite | 1.0 g |
| 5-Methylbenzotriazole | 3.5 g |
| 4-Methyl-4-hydroxymethyl-1-phenyl-pyrazolidone | 13 g |
| Methylhydroquinone | 0.2 g |
| Potassium Hydroxide | 71 g |
| Water | 710 cc |

Figure 1:
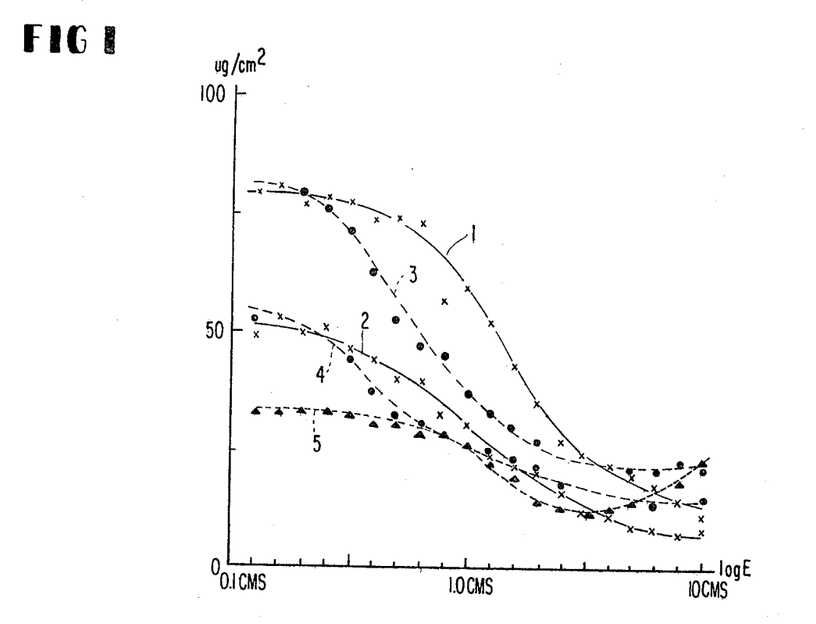
FIG. 1 shows the amounts of silver deposit of reversal image versus exposure amounts (in logarithms).
Figure 2:
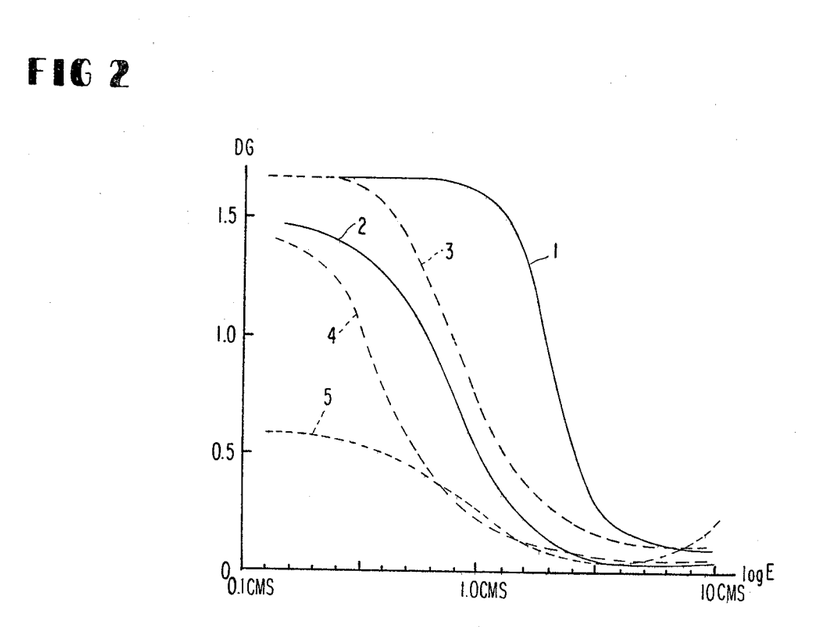
FIG. 2 shows the transmission density of reversal color images obtained by dye transfer, versus exposure amounts (in logarithms).

The density of the image in the image-receiving element was measured to obtain the following results (see FIGS. 1 and 2).

The used dye-releasing redox compound had the following structure:

(M₁)

The optical sensitizers had the following structures:

17.5 g of phenacyl bromide was dissolved in 16 ml of acetone combined with a hot solution prepared by dissolving 10.73 g of nicotinamide in 24 ml of alcohol, and heated for 5 minutes on a steam bath. After cooling, crystals thus formed were collected by filtration and washed with alcohol and benzene to obtain 15.5 g of slightly yellow crystals (3-carbamoyl-1-phenacyl-pyridinium bromide).

Elemental Analysis for $C_{14}H_{13}O_2N_2Br$: Found (%): C: 52.1; H: 4.2; N: 8.8; Br: 3.10 mmol/g; Calculated (%): C: 52.4; H: 4.1; N: 8.7; Br: 3.11 mmol/g.

The above-described 3-carbamoyl-1-phenacyl-pyridinium bromide was dissolved in water to obtain a 0.803% (0.025 M) solution thereof. For the purpose of comparison, formyl-p-tolylhydrazine described in U.S. Pat. No. 3,227,552 was dissolved in methanol to prepare a 1.662% (0.10 M) solution thereof, and 1-(2-formylethyl)-2-methylbenzothiazolium bromide:

described in U.S. Pat. No. 3,734,738 was dissolved in methanol to prepare a 1.43% (0.050 M) solution thereof.

FIGS. 1 and 2 show the characteristics of the reversal image formed by the novel nucleating agent of the present invention (Compound 54) in comparison with that of a known nucleating agent.

In FIG. 2 the density values (transmission density values) of positive transferred images in the image-receiving elements are plotted on the ordinate with the exposure amount (Log exposure amounts) on the abscissa. In FIG. 1, the amounts of silver deposit (μg/cm) in the light-sensitive elements are plotted on the ordinate with the exposure amounts on abscissa. The relationships between each curve and the kind of nucleating agent are tabulated in the following table.

From these results, it has been demonstrated that the nucleating agent of the present invention can simultaneously provide high maximum density and low minimum density when added in lower amounts as com- pared with known compounds and tend less to provide negative (reversed) images upon excessive exposures.

| Curve | Compound | Amount of Added Nucleating Agent (mmol/mol Ag) |
|---|---|---|
| 1 | (n)C$_{16}$H$_{33}$NHCO— | 2.00 |
| 2 |  | 0.71 |
| 3 | | 8.00 |
| 4 | CH$_3$—⟨ ⟩—NHNHCHO | 4.00 |
| 5 |  | 4.00 |

EXAMPLE 2

Light-sensitive elements were prepared under the same conditions as in Example 1 except changing the nucleating agent. After development processing under the same conditions, the results shown in Table 1 were obtained. These results show that reversal images with good characteristics can be obtained. In contrast, the compounds as illustrated below did not provide suitable reversal images.

(a)

(a) [structure with 2-CH$_3$ pyridinium, CH$_3$CO-phenyl, Br$^\ominus$]

(b) [4-CH$_3$ pyridinium, CH$_2$CO-phenyl, Br$^\ominus$]

(c) [2-Br pyridinium, CH$_2$CO-phenyl, Br$^\ominus$]

(d) [4-Br pyridinium, CH$_2$CO-phenyl, Br$^\ominus$]

-continued (e)

(f)  pyridinium-CH$_2$COOC$_2$H$_5$ . Cl$^\ominus$

(g)  pyridinium-CH$_2$CONH$_2$ . Br$^\ominus$ (h)  pyridinium N$^\oplus$—CH$_2$CONHNH$_2$ . Cl$^\ominus$ (i) (CH$_3$)$_3$N$^\oplus$—CH$_2$CONHNH$_2$ . Cl$^\ominus$ (j) (CH$_3$)$_2$S$^\oplus$—CH$_2$—phenyl . Cl$^\ominus$ (k) pyridinium N$^\oplus$—C$_2$H$_5$ . Br$^\ominus$ (l)

TABLE 1
Characteristic Values of Transferred Magenta Dye Images

| | | Photographic Properties | |
|---|---|---|---|
| Compound No. | Amount Added (mmol/mol Ag) | Minimum Density | Maximum Density |
| 1 | 2.0 | 0.03 | 0.72 |
| 7 | 2.0 | 0.03 | 0.94 |
| 8 | 1.4 | 0.03 | 1.25 |
| 9 | 1.4 | 0.05 | 1.34 |
| 12 | 1.4 | 0.04 | 1.30 |
| 17 | 1.4 | 0.03 | 1.23 |
| 19 | 1.4 | 0.03 | 1.18 |
| 20 | 1.4 | 0.03 | 1.07 |
| 23 | 1.4 | 0.03 | 1.11 |
| 25 | 1.4 | 0.04 | 1.17 |
| 27 | 1.4 | 0.03 | 1.20 |
| 29 | 1.4 | 0.03 | 1.02 |
| 32 | 1.4 | 0.04 | 1.46 |
| 33 | 1.4 | 0.05 | 1.41 |
| 34 | 1.4 | 0.04 | 1.29 |
| 35 | 1.4 | 0.04 | 1.40 |
| 36 | 1.4 | 0.04 | 1.50 |
| 37 | 1.4 | 0.03 | 1.43 |
| 39 | 1.4 | 0.04 | 1.53 |
| 40 | 1.4 | 0.04 | 1.52 |
| 42 | 1.4 | 0.04 | 1.64 |
| 43 | 1.4 | 0.04 | 1.65 |
| 44 | 1.4 | 0.04 | 1.68 |

TABLE 1-continued

| | Characteristic Values of Transferred Magenta Dye Images | | |
|---|---|---|---|
| | | Photographic Properties | |
| Compound No. | Amount Added (mmol/mol Ag) | Minimum Density | Maximum Density |
| 46 | 1.4 | 0.04 | 1.42 |
| 47 | 1.4 | 0.03 | 1.28 |
| 48 | 1.4 | 0.03 | 1.29 |
| 50 | 1.4 | 0.03 | 1.34 |
| 52 | 1.4 | 0.04 | 1.43 |
| 54 | 1.4 | 0.04 | 1.68 |
| 56 | 1.4 | 0.04 | 1.47 |
| 57 | 1.4 | 0.04 | 1.42 |
| 58 | 1.4 | 0.04 | 1.44 |
| 59 | 1.4 | 0.04 | 1.45 |
| 60 | 1.4 | 0.03 | 1.20 |
| 61 | 1.4 | 0.04 | 1.51 |
| 62 | 1.4 | 0.04 | 1.53 |
| 63 | 1.4 | 0.04 | 1.57 |
| 65 | 1.4 | 0.04 | 1.41 |
| 66 | 1.4 | 0.03 | 1.37 |
| 69 | 1.4 | 0.03 | 1.19 |
| 71 | 1.4 | 0.03 | 0.81 |
| 72 | 1.4 | 0.03 | 1.56 |
| 73 | 1.4 | 0.04 | 1.27 |
| 79 | 2.8 | 0.02 | 0.56 |
| 80 | 1.4 | 0.04 | 1.67 |
| 81 | 1.4 | 0.04 | 1.58 |
| 82 | 1.4 | 0.03 | 1.42 |
| 83 | 1.4 | 0.05 | 1.69 |
| 84 | 1.4 | 0.06 | 1.68 |
| No nucleating Agent | 0 | 0.02 | 0.06 |

EXAMPLE 3

On a transparent polyethylene terephthalate film base were coated a mordant layer (as a first layer) containing 3.0 g/m² of poly(3- or 4-tri-n-hexylammoniummethyl)styrene chloride and 2.5 g/m² of gelatin, a light-reflecting layer (as a second layer) containing 20 g/m² of titanium white and 2.5 g/m² of gelatin, and a light-intercepting layer (as a third layer) containing 3.0 g/m² of carbon black and 2.0 g/m² of gelatin. Then, the following layers were coated, in sequence, thereon to prepare a diffusion transfer light-sensitive element.

4th Layer:
A layer containing 0.56 g/m² of a cyan dye-releasing redox compound and 1.5 g/m² of gelatin.

5th Layer:
A red-sensitive emulsion layer formed by coating a solution prepared by adding in order, to a red-sensitive internal latent image-forming silver halide emulsion, $1.0 \times 10^{-3}$ mol/mol silver of a methyl alcohol solution of the aforesaid nucleating agent (Compound 54), a methanol solution of 2-sulfo-5-n-pentadecylhydroquinone potassium salt, and an aqueous solution of 4-hydroxy-6-methyl-1,3,3a,7-tetrazaindene sodium salt, in an amount of 1.5 g/m² silver and 1.5 g/m² gelatin.

6th Layer:
An interlayer containing 0.8 g/m² of 2,5-di-t-pentadecylhydroquinone and 1.3 g/m² gelatin.

7th Layer:
A layer containing 0.65 g/m² of a magenta dye-releasing redox compound and 1.2 g/m² of gelatin.

8th Layer:
A green-sensitive emulsion layer formed by coating a solution prepared by adding in order, to a green-sensitive internal latent image-forming silver halide emulsion, $1.0 \times 10^{-3}$ mol/mol silver of a methyl alcohol solution of the aforesaid nucleating agent (Compound 54), a methanol solution of 2-sulfo-5-n-pentadecylhydroquinone potassium salt, and an aqueous solution of 4-hydroxy-6-methyl-1,3,3a,7-tetrazaindene sodium salt, in an amount of 1.35 g/m² silver and 1.4 g/m² of gelatin.

9th Layer:
An interlayer containing 0.8 g/m² of 2,5-di-t-pentadecylhydroquinone and 1.3 g/m² of gelatin.

10th Layer:
A layer containing 0.75 g/m² of a yellow dye-releasing redox compound and 1.4 g/m² of gelatin.

11th Layer:
A blue-sensitive emulsion layer formed by coating a solution prepared by adding in order, to a blue-sensitive internal latent image-forming silver halide emulsion, a methanol solution of a nucleating agent, 1-[4-(2-formylhydrazino)phenyl]-3-phenylthiourea, a methanol solution of 2-sulfo-5-n-pentadecylhydroquinone potassium salt, and an aqueous solution of 4-hydroxy-6-methyl-1,3,3a,7-tetrazaindene sodium salt, in an amount of 1.5 g/m² of silver and 1.5 g/m² of gelatin.

12th Layer:
A protective layer containing 0.10 g/m² of 2,5-di-t-pentadecylhydroquinone and 1.3 g/m² of gelatin.

These layers were hardened with 1,3-bis(vinylsulfonyl)-2-propanol.

The dye-releasing redox compounds used were as follows.

Cyan

Magenta

Yellow

The optical sensitizers used were as follows.
Red-Sensitive:

Green-Sensitive:
A pair of the same sensitizers as used in Example 1.
Blue-Sensitive:

Separately, there was prepared a spreading sheet having coated on a transparent polyethylene terephthalate film base a 7-μ thick neutralizing layer (as a first layer) containing 17 g/m² of polyacrylic acid, 0.06 g/m² of N-hydroxysuccinimidobenzenesulfonate, and 0.5 g/m² of ethylene glycol, a 2-μ thick timing layer of cellulose acetate (acetylation degree: 54) (as a second layer), and a 4-μ thick timing layer of vinylidene chloride/acrylic acid copolymer latex (as a third layer).

The light-sensitive element was subjected to stepwise color separation exposure for sensitometry, and placed face to face with the spreading sheet, followed by spreading a processing solution therebetween in a liquid thickness of 80μ at 25° C. Thus, gradual formation of color-separated positive images were observed. One hour after processing, the density values in neutral scale portions were measured to obtain the results shown in Table 2.

TABLE 2

| | Light for Measuring Density | | |
|---|---|---|---|
| | Blue | Green | Red |
| Maximum Density | 1.80 | 1.95 | 2.05 |
| Minimum Density | 0.22 | 0.26 | 0.34 |
| Sensitivity (exposure Index) | 120 | 120 | 120 |

A processing solution prepared by adding 150 g of carbon black to the processing solution used in Example 1 was used.

While the invention has been described in detail and with reference to specific embodiments thereof, it will be apparent to one skilled in the art that various changes and modifications can be made therein without departing from the spirit and scope thereof.

What is claimed is:

1. A process for developing a light-sensitive material comprising a support having thereon at least one unfogged internal latent image-forming silver halide photographic emulsion layer for producing direct positive images which comprises, after imagewise exposure, developing the light-sensitive material with an alkaline solution of a developing agent in the presence of about $1 \times 10^{-4}$ to $6 \times 10^{-3}$ mole per mole of silver halide of a compound represented by the formula I which is capable of selectively forming latent images in the inner portions of said silver halide upon development:

wherein Y represents an acyl group or a cyano group and said acyl group and the 3-, 4- or 5-position of the pyridinium ring may be optionally substituted, with the proviso that said acyl group does not comprise a sulfonyl group.

2. The process of claim 1, wherein said compound of the formula I is substituted at the 3- or the 5-position with an electron attracting group.

3. The process of claim 2, wherein said electron attracting group is a halogen atom, a trihalomethyl group, a cyano group, a carbamoyl group of the formula —CONR³R⁴ (wherein R³ and R⁴ each represents a halogen atom, an alkyl group, an aryl group or a heterocyclic group containing 1 to 20 carbon atoms or R³ and R⁴ combine to form a 5- or 6-membered ring which may be substituted), a carboxylic acid ester group of the formula —COOR⁵ (wherein R⁵ represents an alkyl group, an aryl group or a heterocyclic group containing up to 20 carbon atoms and may be substituted), an acyl group of the formula —COR⁶ (wherein R⁶ represents a hydrogen atom, a hydroxy group, an alkyl group, an aryl group, a heterocyclic group, an amino group, an alkoxy group, an aryloxy group, or a heterocyclic oxy group, said groups containing up to 20 carbon atoms and may be optionally substituted), a sulfamoyl group of the formula —SO₂NR³R⁴ (wherein R³ and R⁴ are defined as above), a sulfonyl group of the formula —SO₂R⁶ (wherein R⁶ is defined as above), an acylamino group of the formula —NHCOR⁷ (wherein R⁷ represents an alkyl group, an aryl group, a heterocyclic group, or an amino group containing up to 20 carbon atoms and may be optionally substituted), a carbonamido group of the formula —NHCOR¹³ (wherein R¹³ represents an alkyl group containing 1 to 21 carbon atoms or an aryl group containing 6 to 20 carbon atoms), a sulfonamido group of the formula —NHSO₂R¹⁴ (wherein R¹⁴ represents an aryl group containing 6 to 20 carbon atoms), an aryl group containing 6 to 20 carbon atoms, an alkyl group containing 1 to 22 carbon atoms, an alkenyl group containing 2 to 10 carbon atoms, or a 5- or 6-membered nitrogen-containing heterocyclic ring.

4. The process of claim 2, wherein said electron attracting substituent is a substituent having a carbonyl group connected to the 3-position of the pyridinium ring.

5. The process of claim 1, wherein said compound of the formula I is formed upon development from compound of the formula II:

wherein X represents an anion, Y represents an acyl group or a cyano group and the acyl group and the 3-, 4- or 5-position of the pyridinium ring may be optionally substituted.

6. The process of claim 5, wherein said compound of the formula I is formed upon development from a compound of the formula III or IV:

wherein n is 0, 1, 2 or 3 and $R^1$, which may be the same or different, represents a substituent at the 3-, 4- or 5-position selected from a trihalomethyl group, a cyano group, a carbamoyl group, a carboxylic acid ester group, a carbonamido group, a sulfonamido group, an acyl group, a sulfonyl group, a sulfamoyl group, an acylamino group, an aryl group, a non-α-hydrogen containing alkyl group, an alkenyl group or a heterocyclic ring, or a substituent at the 3- or 5-position selected from an α-hydrogen-containing alkyl group and a halogen atom, and $R^2$ represents an aryl group, a heterocyclic group or an alkyl group.

7. The process of claim 5, wherein said compound of the formula II is present in an emulsion layer of the light-sensitive photographic material.

8. The process of claim 5, wherein said compound of the formula II is present in a developer solution.

9. The process of claim 6, wherein $R^1$ is an electron attracting group and is present in at least the 3-position.

10. The process of claim 9, wherein said electron attracting group is a halogen atom, a trihalomethyl group, a cyano group, a carbamoyl group of the formula $—CONR^3R^4$ (wherein $R^3$ and $R^4$ each represents a halogen atom, an alkyl group, an aryl group or a heterocyclic group conatining 1 to 20 carbon atoms or $R^3$ and $R^4$ combine to form a 5- or 6-membered ring which may be substituted), a carboxylic acid ester group of the formula $—COOR^5$ (wherein $R^5$ represents an alkyl group, an aryl group or a heterocyclic group containing up to 20 carbon atoms and may be substituted), an acyl group of the formula $—COR^6$ (wherein $R^6$ represents a hydrogen atom, a hydroxy group, an alkyl group, an aryl group, a heterocyclic group, an amino group, an alkoxy group, an aryloxy group, or a heterocyclic oxy group, said groups containing up to 20 carbon atoms and may be optionally substituted), a sulfamoyl group of the formula $—SO_2NR^3R^4$ (wherein $R^3$ and $R^4$ are defined as above), a sulfonyl group of the formula $—SO_2R^6$ (wherein $R^6$ is defined as above), an acylamino group of the formula $—NHCOR^7$ (wherein $R^7$ represents an alkyl group, an aryl group, a heterocyclic group, or an amino group containing up to 20 carbon atoms and may be optionally substituted), a carbonamino group of the formula $—NHCOR^{13}$ (wherein $R^{13}$ represents an alkyl group containing 1 to 21 carbon atoms or an aryl group containing 6 to 20 carbon atoms), a sulfonamido group of the formula $—NHSO_2R^{14}$ (wherein $R^{14}$ represents an aryl group containing 6 to 20 carbon atoms), an aryl group containing 6 to 20 carbon atoms, an alkyl group containing 1 to 22 carbon atoms, an alkenyl group containing 2 to 10 carbon atoms, or a 5- or 6-membered nitrogen-containing heterocyclic ring.

11. The process of claim 9, wherein said electron attracting group contains a carbonyl group linked to the 3-position of the pyridinium ring.

12. The process of claim 1, wherein said internal latent image-forming emulsion layer is associated with a dye providing compound which is capable of reacting with the oxidation product of the developing agent to form a dye image.

13. The process of claim 12, wherein said developer is an aromatic primary amine color developing agent.

14. The process of claim 12, wherein said dye providing compound is a dye releasing redox compound.

15. The process of claim 1, wherein said internal latent image forming emulsion layer is associated with a color coupler.

16. The process of claims 1, 5 or 6, wherein said pyridinium ring is substituted at the 3-position by a cyano group.

17. The process of claims 1, 5 or 6, wherein said pyridinium ring is substituted at the 3-position with a halogen atom.

18. The process of claims 1, 5 or 6, wherein said pyridinium ring is unsubstituted.

19. The process of claims 1, 5 or 6, wherein said pyridinium ring is substituted at the 3-position by a carbamoyl group.

20. The process of claim 7, wherein said compound contains a ballast group.

21. A photographic light-sensitive material comprising a support having provided thereon at least one unfogged internal latent image-forming silver halide photographic emulsion layer for producing direct positive images associated with a compound of the formula II:

in an amount of about $1 \times 10^{-4}$ to $6 \times 10^{-3}$ mole per mole of silver halide wherein X represents an anion, Y represents an acyl group or a cyano group an the acyl group and the 3-, 4- or 5-position of the pyridinium ring may be optionally substituted, with the proviso that said acyl group does not comprise a sulfonyl group.

22. The photographic material of claim 21, wherein said compound is represented by the formula III or IV:

wherein n is 0, 1, 2 or 3 and $R^1$ represents a halogen atom, a trihalomethyl group, a cyano group, a carbamoyl group, a carboxylic acid ester group, a carbonamido group, a sulfonamido group, an acyl group, a sulfonyl group, a sulfamoyl group, an acylamino group, an aryl group, an alkyl group, an alkenyl group and a heterocyclic ring and $R^2$ represents an aryl group, a heterocyclic group or an alkyl group.

23. The photographic material of claims 21 or 22, wherein said emulsion layer is further associated with a color-providing material to form a dye image.

24. The color photographic material of claim 23, wherein said color-providing material is color-forming coupler.

25. The color photographic material of claim 23, wherein said color-providing material is diffusible-dye-releasing redox compound.

* * * * *

UNITED STATES PATENT AND TRADEMARK OFFICE
CERTIFICATE OF CORRECTION

PATENT NO. : 4,324,855
DATED : April 20, 1982
INVENTOR(S) : Heinz H. Dickmann, et al.

It is certified that error appears in the above-identified patent and that said Letters Patent are hereby corrected as shown below:

Claims 1-6, line 1 of each claim, delete "according to claim 1".

Signed and Sealed this

Twelfth Day of March 1985

[SEAL]

Attest:

DONALD J. QUIGG

Attesting Officer

Acting Commissioner of Patents and Trademarks